(12) United States Patent
Girard et al.

(10) Patent No.: US 8,366,687 B2
(45) Date of Patent: Feb. 5, 2013

(54) INJECTION ACCESS PORT WITH CHAMFERED TOP HAT SEPTUM DESIGN

(75) Inventors: Mark Girard, Waltham, MA (US); Todd Beaupre, Reading, MA (US); Benjamin Bell, Haverhill, MA (US); Mark Wolfson, Wellesley, MA (US); Richard Nisil, Blackstone, MA (US); Jeffrey J. Crowley, Milford, MA (US); Nathan Murphy, Westborough, MA (US)

(73) Assignee: Angio Dynamics, Latham, NY (US)

( * ) Notice: Subject to any disclaimer, the term of this patent is extended or adjusted under 35 U.S.C. 154(b) by 865 days.

(21) Appl. No.: 10/752,257

(22) Filed: Jan. 6, 2004

(65) Prior Publication Data

US 2005/0148957 A1    Jul. 7, 2005

(51) Int. Cl.
*A61M 37/00*    (2006.01)
(52) U.S. Cl. .................................. 604/288.02; 604/175
(58) Field of Classification Search ............. 604/288.02, 604/175; 156/86; 219/105
See application file for complete search history.

(56) References Cited

U.S. PATENT DOCUMENTS

| | | | |
|---|---|---|---|
| 3,159,175 | A | 12/1964 | Macmillan |
| 3,477,438 | A | 11/1969 | Allen et al. |
| 3,525,357 | A | 8/1970 | Koreski |
| 3,541,438 | A | 11/1970 | Nelsen et al. |
| 3,669,323 | A | 6/1972 | Harker et al. |
| 3,674,183 | A | 7/1972 | Venable et al. |
| 3,811,466 | A | 5/1974 | Ohringer |
| 3,853,127 | A | 12/1974 | Spademan |
| 3,955,594 | A | 5/1976 | Snow |
| 3,971,376 | A | 7/1976 | Wichterle |
| 4,143,853 | A | 3/1979 | Abramson |
| 4,447,237 | A | 5/1984 | Frisch et al. |

(Continued)

FOREIGN PATENT DOCUMENTS

| CA | 2399057 | 8/2001 |
|---|---|---|
| EP | 0128525 | 12/1984 |

(Continued)

OTHER PUBLICATIONS

International Search Report and Written Opinion mailed Mar. 29, 2005 for International Application No. PCT/US2004/043229 (9 pages).

(Continued)

*Primary Examiner* — Kevin C Sirmons
*Assistant Examiner* — Phillip Gray
(74) *Attorney, Agent, or Firm* — Ryan D. Artis

(57) ABSTRACT

An access port comprises a housing with a first opening and a self sealing septum sealing the first opening, the septum including an attachment portion for securing the septum to the housing, the attachment portion including a chamfer which, when the septum is mounted within the housing is subject to a force oriented substantially perpendicularly with respect to a plane of the outer surface, the chamfered portion redirecting a portion of the force to compress the outer surface. A septum for an access port comprises an attachment portion for abutting a septum seat of the access port and an operative surface permitting penetration by a needle and resealing itself after removal of the needle in combination with a chamfered portion providing a transition between the attachment portion and the operative surface, the chamfered portion re-directing a component of a force applied to the chamfered portion to compress the operative surface.

17 Claims, 2 Drawing Sheets

U.S. PATENT DOCUMENTS

| | | | |
|---|---|---|---|
| 4,543,088 A | 9/1985 | Bootman et al. | |
| 4,610,665 A | 9/1986 | Matsumoto et al. | |
| 4,692,146 A | 9/1987 | Hilger | |
| 4,772,270 A * | 9/1988 | Wiita et al. | 604/175 |
| 4,781,680 A | 11/1988 | Redmond et al. | |
| 4,802,885 A | 2/1989 | Weeks et al. | |
| 4,857,053 A | 8/1989 | Dalton | |
| 4,886,501 A | 12/1989 | Johnston et al. | |
| 4,886,502 A | 12/1989 | Poirier et al. | |
| 4,892,518 A | 1/1990 | Cupp et al. | |
| 4,897,081 A | 1/1990 | Poirier et al. | |
| 4,904,241 A * | 2/1990 | Bark | 604/288.02 |
| 4,908,029 A | 3/1990 | Bark et al. | |
| 4,929,236 A | 5/1990 | Sampson | |
| 5,009,391 A | 4/1991 | Steigerwald | |
| 5,009,644 A | 4/1991 | McDonald | |
| 5,045,060 A | 9/1991 | Melsky et al. | |
| 5,053,013 A | 10/1991 | Ensimger et al. | |
| 5,059,186 A | 10/1991 | Yamamoto et al. | |
| 5,069,206 A | 12/1991 | Crosbie | |
| 5,084,015 A | 1/1992 | Moriuchi | |
| 5,092,849 A * | 3/1992 | Sampson | 604/175 |
| 5,129,891 A | 7/1992 | Young | |
| 5,137,529 A | 8/1992 | Watson et al. | |
| 5,147,483 A * | 9/1992 | Melsky et al. | 156/86 |
| 5,167,638 A | 12/1992 | Felix et al. | |
| 5,180,365 A | 1/1993 | Ensminger et al. | |
| 5,205,834 A | 4/1993 | Moorehead et al. | |
| 5,242,415 A | 9/1993 | Kantrowitz et al. | |
| 5,249,598 A | 10/1993 | Schmidt | |
| 5,263,930 A | 11/1993 | Ensminger | |
| 5,281,199 A | 1/1994 | Ensminger et al. | |
| 5,312,337 A | 5/1994 | Flaherty et al. | |
| 5,318,545 A | 6/1994 | Tucker | |
| 5,350,360 A | 9/1994 | Ensminger et al. | |
| 5,352,204 A | 10/1994 | Ensminger | |
| 5,356,381 A | 10/1994 | Ensminger et al. | |
| 5,387,192 A | 2/1995 | Glantz et al. | |
| 5,396,925 A | 3/1995 | Poli et al. | |
| 5,399,168 A | 3/1995 | Wadsworth et al. | |
| 5,417,656 A | 5/1995 | Ensminger et al. | |
| 5,423,334 A | 6/1995 | Jordan | |
| 5,453,097 A | 9/1995 | Paradis | |
| 5,476,451 A | 12/1995 | Ensminger et al. | |
| 5,520,643 A | 5/1996 | Ensminger et al. | |
| 5,527,277 A | 6/1996 | Ensminger et al. | |
| 5,527,278 A | 6/1996 | Ensminger et al. | |
| 5,531,684 A | 7/1996 | Ensminger et al. | |
| 5,542,923 A | 8/1996 | Ensminger et al. | |
| 5,554,117 A | 9/1996 | Ensminger et al. | |
| 5,556,381 A | 9/1996 | Ensminger et al. | |
| 5,558,641 A | 9/1996 | Galntz et al. | |
| 5,562,618 A | 10/1996 | Cai et al. | |
| 5,607,393 A | 3/1997 | Ensminger et al. | |
| 5,613,945 A | 3/1997 | Cai et al. | |
| 5,662,616 A | 9/1997 | Bousquet | |
| 5,707,357 A | 1/1998 | Mikhail et al. | |
| 5,741,228 A | 4/1998 | Lambrecht et al. | |
| 5,755,780 A | 5/1998 | Finch et al. | |
| 5,792,104 A | 8/1998 | Speckman et al. | |
| 5,792,123 A | 8/1998 | Ensminger | |
| 5,797,886 A | 8/1998 | Roth et al. | |
| 5,814,016 A | 9/1998 | Valley et al. | |
| 5,848,989 A | 12/1998 | Villani | |
| 5,879,322 A | 3/1999 | Lattin et al. | |
| 5,882,341 A | 3/1999 | Bousquet | |
| 5,897,528 A | 4/1999 | Schultz | |
| 5,906,596 A | 5/1999 | Tallarida | |
| 5,911,706 A | 6/1999 | Estabrook et al. | |
| 5,941,856 A | 8/1999 | Kovacs et al. | |
| 5,944,688 A | 8/1999 | Lois | |
| 5,944,698 A | 8/1999 | Fischer et al. | |
| 5,954,687 A | 9/1999 | Baudino | |
| 5,954,691 A | 9/1999 | Prosl | |
| 5,961,497 A | 10/1999 | Larkin | |
| 5,989,216 A * | 11/1999 | Johnson et al. | 604/288.02 |
| 6,056,717 A | 5/2000 | Finch et al. | |
| 6,086,555 A | 7/2000 | Eliasen et al. | |
| 6,099,508 A | 8/2000 | Bousquet | |
| 6,152,909 A | 11/2000 | Bagaoisan et al. | |
| 6,190,352 B1 | 2/2001 | Haarala et al. | |
| 6,210,366 B1 | 4/2001 | Sanfilippo | |
| 6,287,293 B1 | 9/2001 | Jones et al. | |
| 6,306,124 B1 | 10/2001 | Jones et al. | |
| 6,527,754 B1 | 3/2003 | Tallarida et al. | |
| 6,592,571 B1 | 7/2003 | Verbeek et al. | |
| 6,610,031 B1 | 8/2003 | Chin | |
| 6,726,063 B2 | 4/2004 | Stull et al. | |
| 6,962,577 B2 | 11/2005 | Tallarida et al. | |
| 7,033,339 B1 | 4/2006 | Lynn | |
| 2003/0141477 A1* | 7/2003 | Miller | 251/149.1 |

FOREIGN PATENT DOCUMENTS

| | | |
|---|---|---|
| EP | 0343910 | 11/1989 |
| EP | 0366814 | 5/1990 |
| EP | 0858814 | 8/1998 |
| FR | 2508008 | 12/1982 |
| FR | 2809315 | 11/2001 |
| GB | 0966137 | 8/1964 |
| GB | 2102398 | 2/1983 |
| WO | WO-92/06732 | 4/1992 |
| WO | WO-94/05351 | 3/1994 |
| WO | WO-95/16480 | 6/1995 |
| WO | WO-97/01370 | 1/1997 |
| WO | WO-97/23255 | 7/1997 |
| WO | WO-97/26931 | 7/1997 |
| WO | WO-98/18506 | 8/1997 |
| WO | WO-99/42166 | 8/1999 |
| WO | WO-00/12171 | 3/2000 |
| WO | WO-00/16844 | 3/2000 |
| WO | WO-00/44419 | 8/2000 |
| WO | WO 2005/068009 A1 | 7/2005 |

OTHER PUBLICATIONS

International Preliminary Report on Patentability mailed Jul. 10, 2006 for International Application No. PCT/US2004/043229 (7 pages).

* cited by examiner

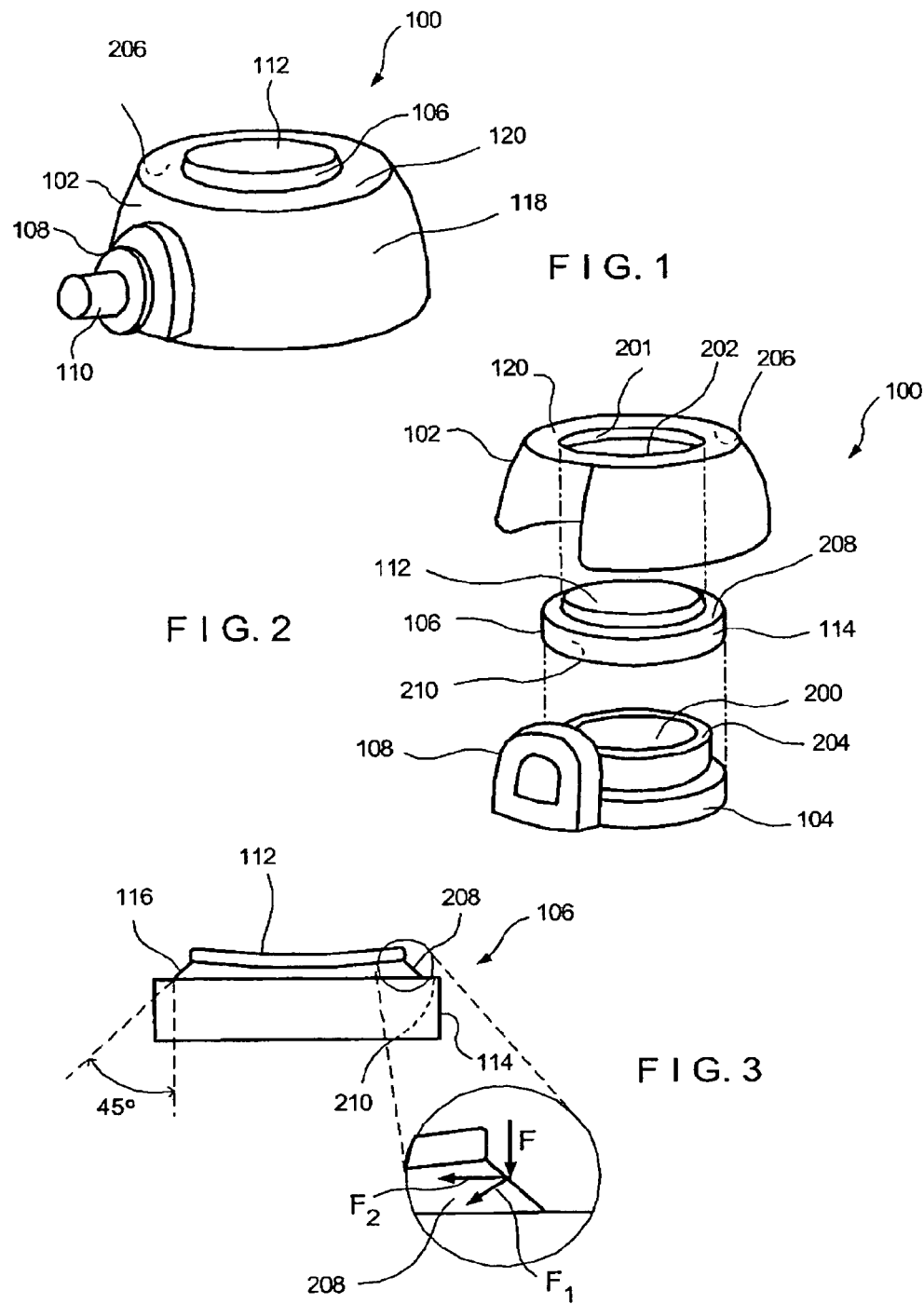

INJECTION ACCESS PORT WITH CHAMFERED TOP HAT SEPTUM DESIGN

BACKGROUND OF THE INVENTION

Medical procedures for the treatment of chronic diseases often require repeated and prolonged access to a patient's vascular system to inject therapeutic compounds and/or to sample or treat the patient's blood. Certain procedures are repeated often enough that it is impractical and dangerous to insert and remove the catheter and the needle from the patient's vein at every session. Many patients are thus fitted with a semi permanent catheter to permit repeated access to the patient's vascular system.

Semi-permanently implanted catheters are generally designed to be as small and thin as possible, to simplify the insertion procedure and to reduce discomfort to the patient. Access to such a catheter is typically provided by one or more ports, which are in fluid connection with the catheter and thus with the patient's vascular system. The port or ports generally have a very thin profile, so they may be implanted in the patient with a minimum of discomfort. In most cases, such a port is implanted subcutaneously, in a pocket formed surgically in the patient's chest or arm so that it lies just under the skin, in a location that is easily accessible to medical personnel. More specifically, a septum of the port is positioned just under the skin so that therapeutic agents may be injected into the port through the skin and through the surface of the septum.

Insertion of therapeutic agents into the catheter is typically carried out by injecting the fluid through the septum of the port, using the needle of a syringe or a similar device. The septum includes at least one surface that is capable of resisting damage cause by multiple piercings from the needle, while re-sealing itself after the needle is withdrawn. The service life of such ports is therefore limited by the durability of the septum. After a certain number of punctures, the septum becomes damaged and is no longer able to re-seal itself. Fluids flowing in the catheter, such as blood, can then leak from the septum necessitating replacement of the port and possibly of the entire catheter. This procedure involves surgically opening the subcutaneous pocket, removing the damaged port from the catheter, and reinserting a new port with an undamaged septum. Replacing the port adds considerable expense, inconvenience and discomfort to the procedure and increases the risk of infections and other complications.

SUMMARY OF THE INVENTION

In one aspect, the present invention is directed to an access port comprising a housing with a first opening formed therein and a septum mounted within the housing sealing the first opening, the septum including an outer surface covering the first opening and self-sealing after penetration by a needle and an attachment portion for securing the septum to the housing, the attachment portion including a chamfer which, when the septum is mounted within the housing is subject to a force oriented substantially perpendicularly with respect to a plane of the outer surface, the chamfered portion redirecting a portion of the force to compress the outer surface.

The present invention is further directed to a septum for an access port comprises an attachment portion adapted to abut a septum seat of the access port and an operative surface adapted to permit penetration by a needle and resealing itself after removal of the needle in combination with a chamfered portion providing a transition between the attachment portion and the operative surface, the chamfered portion re-directing a component of a force applied to the chamfered portion to compress the operative surface.

BRIEF DESCRIPTION OF THE DRAWINGS

FIG. 1 is a diagram showing a perspective view of a injection access port having a septum according to an embodiment of the present invention;

FIG. 2 is a diagram showing an exploded view of the injection access port shown in FIG. 1;

FIG. 3 is a side elevation view of the septum according to an exemplary embodiment of the invention;

DETAILED DESCRIPTION

Figure 4:
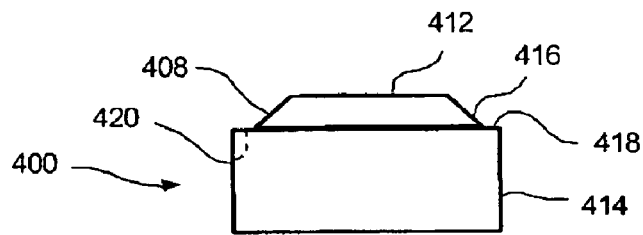
FIG. 4 is a side elevation view of the septum according to another embodiment of the invention.

The present invention may be further understood with reference to the following description and the appended drawings, wherein like elements are referred to with the same reference numerals. The invention is related to medical devices used to introduce fluids into a venous catheter. Specifically, the devices according to the invention are used to increase the useful life of venous ports that may be implanted in a patient to interface with an implanted venous catheter. However, those skilled in the art will understand that the present invention is equally applicable to a wide range of applications in which a port with puncturing a self-sealing septum is implanted in the body. For example, although the invention is described for use with a port for the injection of fluids, the port may just as well be used to withdraw fluids with no change in structure.

As described above, catheters are often semi-permanently implanted to facilitate repeated access to a patient's vascular system. Such catheters may comprise a flexible elongated portion that extends through tissue to enter a blood vessel or other organ. The proximal end of the catheter may be connected to a port placed subcutaneously (e.g., in the chest or the arm) to provide access to the catheter.

The port allows fluids (e.g., chemotherapy agents, blood products, nutrients, therapeutic agents etc.) to be introduced into the patient's vascular system via a syringe or other similar device. The port is a thin element generally connected directly to the catheter through an outlet and having an inlet opening positioned so as to remain substantially flush with the patient's skin after implantation. When not in use, the inlet opening is sealed to prevent blood and other fluids from leaking from the catheter, and at the same time to prevent contaminants from entering into the catheter. To that end, septa have been used to cover and seal the inlet openings of such ports. Such a septum generally comprises a flexible membrane that overlies the inlet opening and seals it with the material forming the septum being selected for its ability to continue sealing the port even after repeated punctures by a needle. For example, silicone or other elastomeric materials have been used to form such septa.

In normal use, the septum is punctured with a needle whenever it is necessary to inject a fluid into the port. Over time, the cumulative damage degrades the material forming the septum so that, after being punctured a sufficient number of times, the septum is unable to re-seal itself after withdrawal of the needle. When the septum is still new, the elastic properties of the membrane tend to "bunch up" or push together the edges of the hole left in the membrane by the puncture. As the membrane is used and the number of holes formed therein increases, the amount of elastic membrane material present around new punctures to close the edges thereof decreases until new holes can no longer be fully closed. At this point, leakage through the operative membrane of the septum begins.

The undesirable result described above is exacerbated if the membrane of the septum is placed under tension as the openings left by punctures are stretched when the membrane is under tension. In addition, tension may tear the membrane around the holes, so that over time the puncture openings become larger and may tear through the membrane. The number of punctures that a septum may withstand depends on the size of the port, the material used, and the size of needles used to inject fluids therethrough. As would be expected, larger needles cause more damage while a larger surface area septum provides more room to spread out the punctures. High quality ports may withstand around 10,000 punctures before replacement is necessitated.

Exemplary embodiments of a septum according to the present invention improve the durability of the corresponding venous port by reducing degradation of the septum due to large numbers of punctures. As will be described in greater detail, an increase in puncture damage resistance is obtained by applying a compressive force to the septum membrane. The compressive force pushes together the edges of individual puncture holes and assists the elastic properties of the membrane in sealing such holes. According to the present invention, the improvement to the membrane forming the operative surface of the septum allows an increase in the number of punctures that can be withstood by the septum before excessive leakage requires replacement. Thus, the incidence of surgical procedures required to replace the port or the entire catheter is reduced.

FIGS. 1 and 2 show, respectively, a perspective view and an exploded view of a venous port having a septum according to an embodiment of the present invention. According to the exemplary embodiment, the port 100 is designed to fit subcutaneously in a pocket surgically created in the patient's chest, arm or other suitable location with a needle piercing membrane facing outward. In this embodiment, the housing of the port 100 is formed of two parts, a base 104 and a cover 102. For example, the base 104 and the cover 102 may be secured together frictionally or with a mechanical interlocking connection, to prevent separation of the two components after they have been placed within the patient's body. As would be understood by those skilled in the art, the exact shape of the base 104 and the cover 102 may vary depending on the specific requirements of the port design. Accordingly, the following description is exemplary only and different configurations may be used to achieve the same results as described below.

The base 104 is designed to form a well 200 into injected into which fluid injected into the port 100 is temporarily collected. The well 200 is in fluid communication with an outlet opening 108 of the port 100, which in turn leads to a connection with a catheter (not shown). In one exemplary embodiment, a valve 110 may be placed at the opening of the outlet 108 to prevent undesired flow into or out of the catheter. In this exemplary embodiment, the cover 102 comprises a shroud portion 118 designed to form an outer surface of the port 100, and a top portion 120 defining an inlet opening 202. The top portion 120 is intended to be flush under the patient's skin when the device is implanted, so that a needle can enter the opening 202 after piercing the patient's skin and a septum 106 closing the opening 202. The shroud portion 118 may be shaped to interlock with the outlet portion 108 of the base 104, and may have a cutout portion around the outlet opening 108 and the inlet opening 202 is sized to substantially match the size of a septum 106, so that when the device is assembled, the inlet opening 202 is sealed by the septum 106.

The septum 106 comprises a top membrane 112 that acts as the operative surface of the port 100, through which the therapeutic compounds are injected. The septum 106 may also include an attachment portion 114 to secure the septum 106 in place within the port 100. In the exemplary embodiment, the attachment portion 114 is an annular element that surrounds a periphery of the top membrane 112 extending outward substantially perpendicularly therefrom. According to the present invention, a chamfer portion 208 provides a transition between the operative surface of the membrane 112, and the attachment portion 114. The purpose of the chamfer portion 208 is to apply a compressive force to membrane 112. In the exemplary embodiment, this force is provided by the compression of the septum 106 between the base 104 and the cover 102 when the port 100 is assembled. The shape and orientation of the chamfer portion 208 re-directs the force applied by the assembled components of the port 100 to the septum 106, so that a component of that force acts radially inward along the membrane 112.

More specifically, the chamfer portion 208 of the septum 106 comprises an annular surface 210 formed on an underside of the septum 106 facing the base 104. The annular surface 210 is adapted to overlie and abut a septum seat 204 of the base 104, when the port 100 is assembled. In this manner the septum seat 204 provides an inner support to the chamfer portion 208. When the port 100 is assembled by securing the cover 102 to the base 104, the septum 106 is squeezed between those two components. A bottom bearing surface 206 of the cover 102 presses down on the chamfer portion 208, squeezing it against the septum seat 204. The inner bearing surface 201 of the cover 102 also applies a force radially inward against the chamfer portion 208. The shape of the chamfer portion 208 causes a component of the downward force applied thereto by the inner bearing surface to be re-directed radially inward along the surface of the membrane 112 around the periphery thereof, so that a compressive force is applied to the operative surface of the septum 106. Thus, the chamfer portion 208 gives to the septum a shape similar to that of a top hat.

As shown in FIG. 3, and more clearly illustrated in the enlarged view of the chamfer portion 208, a force F is applied to the chamfer portion 208 when the base 104 and the cover 102 are assembled, with the septum 106 sandwiched therebetween. Since the surface 116 of the chamfer portion 208 is angled with respect to a direction of the force F, a force component F1 acting perpendicular to the surface 116 results. The force F1 can be further divided into horizontal and vertical components to illustrate radially inward component F2 of the force F1. As the force F is applied around the periphery of the surface of the membrane 112, the force component F2 is directed radially inwardly around the circumference of the membrane 112 compressing the membrane 112. As described above, this compressive force acting radially inward on the membrane 112 increases the tolerance of the membrane 112 to puncture damage. In one exemplary embodiment, the chamfer portion 208 comprises a separate angled surface 116 disposed at an angle of approximately 45 degrees to the plane of the operative surface of the membrane 112 and, consequently, to the direction of the force F applied by assembly of the port 100. (Please provide a range for this angle) Those of skill in the art will understand that different angular orientations may be used to optimize the septum 106 for various applications.

The combination of a properly shaped chamfer portion of a septum, and of a venous port housing shaped to hold the septum in place thus provides an increased resistance to damage due to punctures through the septum. Although the present exemplary embodiment describes a port housing formed of two separate components, other housing configurations may be successfully used. According to the invention, when a force is applied to the septum by the components of the assembled venous port, the chamfer portion of the septum may be designed to convert a component of that applied force into a compressive force acting radially inward along the operative surface. Different configurations of the port's housing may thus be devised to apply the proper force to the septum when the port is assembled.

As will be understood by those of skill in the art, additional shapes of the septum's chamfer portion may be used. For example, FIG. 4 shows a septum 400 according to a second embodiment of the invention, where the chamfer portion 408 comprises an angled surface 416 extending directly from a top membrane 412 to an upper surface 418 of an attachment portion 414. The angle at which the surface 416 is oriented may be selected to produce desired characteristics of the septum. When the upper surface 418 and the lower surface 420 are squeezed between a base and a cover of the corresponding venous port, the angled surface 416 causes a component of the vertical force to be applied radially inward to compress the upper membrane 412. As described above, the result is an improved ability of the membrane 412 to re-seal puncture holes therethrough after a needle is withdrawn.

Figure 5:
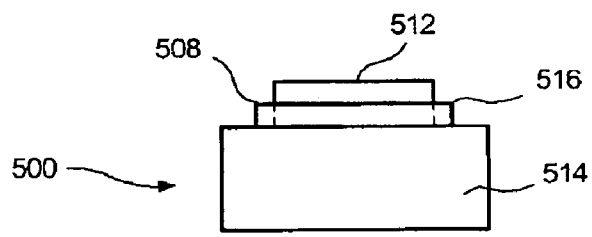
FIG. 5 is a side elevation view of the septum according to a third embodiment of the invention.

A third exemplary embodiment according to the invention is shown in FIG. 5. Here, the transition between an upper membrane 512 of the operative surface and an attachment portion 514 is carried out by a step 516. The precise characteristics of the step 516 may be developed to obtain a desired compression in the membrane 512, and to facilitate the assembly of the corresponding venous port. For example, the step 516 may be substantially rectangular, with surfaces at right angles to the top membrane 512, and to the sides of an attachment portion 514. In an alternative embodiment, the surfaces of the step 516 may be oriented at different angles, and may not be perpendicular and parallel, respectively, to the top and side surfaces of the septum 500.

Figure 6:
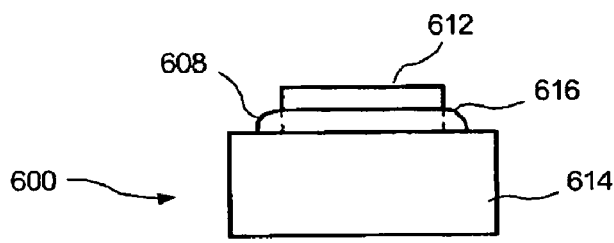
FIG. 6 is a side elevation view of the septum according to a fourth embodiment of the invention.

FIG. 6 shows a side elevation view of a fourth embodiment of a top hat-shaped chamfered septum 600 according to the present invention. In this embodiment, the chamfer portion 608 comprises a curved fillet 616 extending between the top membrane 612 of the operative surface and a surface of the attachment portion 614. In the exemplary embodiment, the curvature of the fillet 616 has a substantially constant radius, however alternative designs may include variable radii to offer more complex curves. The curved fillet 616 is preferably convex, to facilitate transferring to the top surface 612 a compressive component of the force applied during assembly of the septum 600 in the corresponding port. A curved fillet 616 may offer advantages in durability over chamfer portions having more angular features, since fewer angles and edges which concentrate stresses are present in the design.

Figure 7:
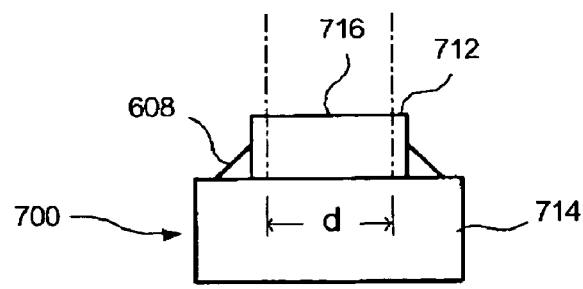
FIG. 7 is a side elevation view of the septum according to a fifth embodiment of the invention.

Additional benefits with respect to the useful life of the septum may be obtained by using an oversized septum, in relation to the inlet opening of the venous port. For example, as illustrated in FIG. 7, a septum 700 may include an operative surface comprising a top membrane 716, which has a larger diameter than the underlying inlet opening of the port. As shown in the diagram, the inlet opening of the corresponding venous port may have a diameter "d" which is smaller than the diameter of the top membrane 716. Thus, when the operative surface of the septum 700 is squeezed into the inlet opening of the port, the side surfaces of the inlet opening of the port will apply a compressive force to the septum 700. To maximize the useful life of the port, the oversized septum may be fitted with any of the chamfer portions described above, so that a compressive force is applied to the top membrane 716.

According to the present invention, the assembly details of the venous port being assembled may dictate some of the design features of the septum. For example, the angle taken by the surfaces of the chamfer portion may vary to match the corresponding surfaces of the port. The various dimensions and orientations of the septum's surfaces also may vary, in accordance with the size and shape of the port in which the septum is used. Accordingly, great latitude may be used within the general shape of the top hat-shaped septum, according to the present invention, to fit the device in an appropriate venous port. As described above, many shapes of chamfer portions may be used to apply a compressive force to the operative surface of the septum, by re-directing a component of the force applied during port assembly. The materials used in forming the septum, as well as cost and ease of assembly considerations may determine which specific design is selected.

The present invention has been described with reference to specific embodiments, and more specifically to a septum used in a venous catheter port. However, other embodiments may be devised that are applicable to other medical devices, without departing from the scope of the invention. Accordingly, various modifications and changes may be made to the embodiments, without departing from the broadest spirit and scope of the present invention as set forth in the claims that follow. The specification and drawings are accordingly to be regarded in an illustrative rather than restrictive illustrative rather than restrictive sense.

What is claimed is:

1. An access port comprising:
   a housing with a first and second openings formed therein; and
   a septum mounted within the housing sealing the first opening, the septum including:
      a solid, disk-shaped operative portion engaging the first opening and self-sealing after penetration by a needle; and
      an annular attachment portion for securing the septum to the housing, the attachment portion being coupled to the operative surface by a chamfered portion which, when the septum is mounted within the housing, is not coplanar with the annular surface and is subject to a force oriented substantially perpendicularly with respect to the annular surface, the chamfered portion redirecting a portion of the force to compress the operative surface in a direction substantially parallel to the annular surface,
   wherein the chamfered portion comprises an elastomeric material extending continuously, without interruption, along a cross-sectional plane, wherein the chamfer is not perpendicular to the operative surface and the annular surface, and wherein the second opening is adapted to connect to a catheter and is substantially perpendicular to the first opening.

2. The access port according to claim 1, wherein a base of the housing forms a septum seat and a cover of the housing secures the septum on the seat so that the attachment portion is compressed therebetween.

3. The access port according to claim 1, wherein the chamfer comprises at least one surface that forms an angle of between 0° and 90° relative to the operative surface and the annular surface.

4. The access port according to claim 3, wherein the at least one angled surface forms a 45 degree angle to the operative surface.

5. The access port according to claim 1, wherein the chamfer comprises a stepped surface extending away from the operative surface.

6. The access port according to claim 1, wherein the chamfer comprises a curved fillet extending away from the operative surface.

7. The access port according to claim 6, wherein the curved fillet has a substantially constant radius of curvature.

8. The access port according to claim 1, wherein the annular surface abuts a septum seat of the housing.

9. The access port according to claim 1, wherein the operative surface comprises a substantially planar membrane overlying the first opening.

10. The access port according to claim 1, wherein the operative surface comprises a membrane which, when unconstrained has a dimension greater than a corresponding dimension of the first opening so that, when placed within the first opening the operative surface is compressed thereby.

11. A septum for an access port, comprising:
an annular attachment portion adapted to abut a septum seat of the access port, the attachment portion including an annular surface;
a solid, disk-shaped operative portion adapted to permit penetration by a needle and resealing itself after removal of the needle, a periphery of the operative surface being radially within a periphery of the annular surface; and
a chamfered portion providing a transition between the annular attachment portion and the operative surface, wherein the chamfered portion comprises an elastomeric material extending continuously, without interruption, along a cross-sectional plane, wherein the chamfered portion is not coplanar with the annular surface and is not perpendicular to the operative surface and the annular surface, and wherein the septum is a unitary body.

12. The septum according to claim 11, wherein the operative surface is sized to substantially overlie an opening of the access port.

13. The septum according to claim 11, wherein the chamfer portion is adapted to apply to the operative surface a radially compressive component of a force applied substantially perpendicularly thereto by assembly of the access port.

14. The septum according to claim 11, wherein the chamfered portion comprises a fillet joining the operative surface to the attachment portion.

15. The septum according to claim 11, wherein the chamfered portion comprises an angled surface that forms an angle of between 0° and 90° joining the operative surface to the attachment portion.

16. The septum according to claim 11, wherein the chamfered portion comprises a stepped surface joining the operative surface to the attachment portion.

17. The septum according to claim 11, wherein the operative surface is formed of a flexible polymeric material.

* * * * *